(12) United States Patent
Wright

(10) Patent No.: US 6,889,688 B1
(45) Date of Patent: May 10, 2005

(54) PORTABLE AIR DELIVERY SYSTEM AND METHOD OF USING SAME

(75) Inventor: Clifford A. Wright, San Diego, CA (US)

(73) Assignee: Medical Device Group, Inc., Poway, CA (US)

(*) Notice: Subject to any disclaimer, the term of this patent is extended or adjusted under 35 U.S.C. 154(b) by 46 days.

(21) Appl. No.: 10/389,869

(22) Filed: Mar. 17, 2003

(51) Int. Cl.[7] .................... A61M 15/00; A61M 16/00
(52) U.S. Cl. .................... 128/200.24; 128/202.27; 128/204.18; 128/205.22; 128/207.18
(58) Field of Search ............................ 242/169, 170, 242/227, 403; 137/355.12, 355.22; 128/200.24, 202.27, 204.18, 205.22, 207.18

(56) References Cited

U.S. PATENT DOCUMENTS

| | | | | |
|---|---|---|---|---|
| 5,381,820 A | * | 1/1995 | Chandler | 137/355.23 |
| 5,826,608 A | * | 10/1998 | Pierce | 137/15.08 |
| 6,065,490 A | * | 5/2000 | Falcone, Jr. | 137/355.23 |
| 6,279,848 B1 | * | 8/2001 | Mead, Jr. | 242/397.3 |
| 6,588,444 B2 | * | 7/2003 | Paplow et al. | 137/15.01 |

* cited by examiner

*Primary Examiner*—Glenn K. Dawson
*Assistant Examiner*—Michael Mendoza
(74) *Attorney, Agent, or Firm*—Fish & Richardson P.C.

(57) ABSTRACT

An air delivery system includes a coupling mechanism that is adapted to be connected between a source of oxygen-enriched air and an air cannula that can be worn by a user. The coupling mechanism includes a spool assembly for paying out and for winding up a predetermined length of tubing coupled between the air cannula and the source of oxygen-enriched air. The spool assembly has a sufficiently low drag factor to allow complete mobility of a user wearing the cannula without causing it to be dislodged during pay out of the predetermined length of tubing and without causing it to be dislodged during take up of the predetermined length of tubing.

9 Claims, 7 Drawing Sheets

PORTABLE AIR DELIVERY SYSTEM AND METHOD OF USING SAME

FIELD OF THE INVENTION

The present invention pertains to an air delivery system and more particularly to a coupling device between an air canister and an air cannula to provide an oxygen dependent user with extensive mobility from the air canister.

BACKGROUND OF THE INVENTION

Patients that require a constant supply of oxygen-enriched air are generally confined to an immediate area of the source of such oxygen-enriched air regardless of whether the source is a hospital air supply system or a simple portable air canister system.

Therefore it would be highly desirable to have a new and improved air supply system that provides ambulatory patients with extensive mobility from their source of oxygen-enriched air whether the source is a hospital air supply system or an air canister system.

One attempt at providing an oxygen dependent user with extensive mobility has been to provide a small lightweight canister that can be easily transported or carried by the user as he or she moves from place to place. While such a system accomplishes it intended purpose, it has not proven to be entirely satisfactory as such a small lightweight canister can only supply a limited amount of oxygen enriched air. Moreover, even though the canister is small and lightweight for many elders even such a lightweight canister is too heavy to be carried while performing ordinary tasks.

Therefore it would be highly desirable to have a new and improved air delivery system that is lightweight and that can be easily carried or transported by an oxygen dependent user to allow the user to move freely in any desired direction relative to a large supply of oxygen enriched air provided in a large, heavy, burdensome air canister.

SUMMARY OF THE INVENTION

An air delivery system includes a coupling mechanism that is adapted to be connected between a source of oxygen-enriched air and an air cannula that can be worn by a user. The coupling mechanism includes a spool assembly for paying out and for winding up a predetermined length of tubing coupled between the air cannula and the source of oxygen-enriched air. The spool assembly has a sufficiently low drag factor to allow complete mobility of a user wearing the cannula without causing the cannula to be dislodged during pay out of the predetermined length of tubing and without causing the cannula to be dislodged during take up of the predetermined length of tubing. In use, an oxygen dependent user attaches the coupling mechanism to his or her belt, connects the coupling mechanism between a source of oxygen-enriched air and a user worn air cannula and then walk freely in any direction from the source of oxygen-enriched air without causing the air cannula to be dislodged.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein.

DETAILED DESCRIPTION OF THE PREFERRED EMBODIMENT OF THE INVENTION

Figure 1:
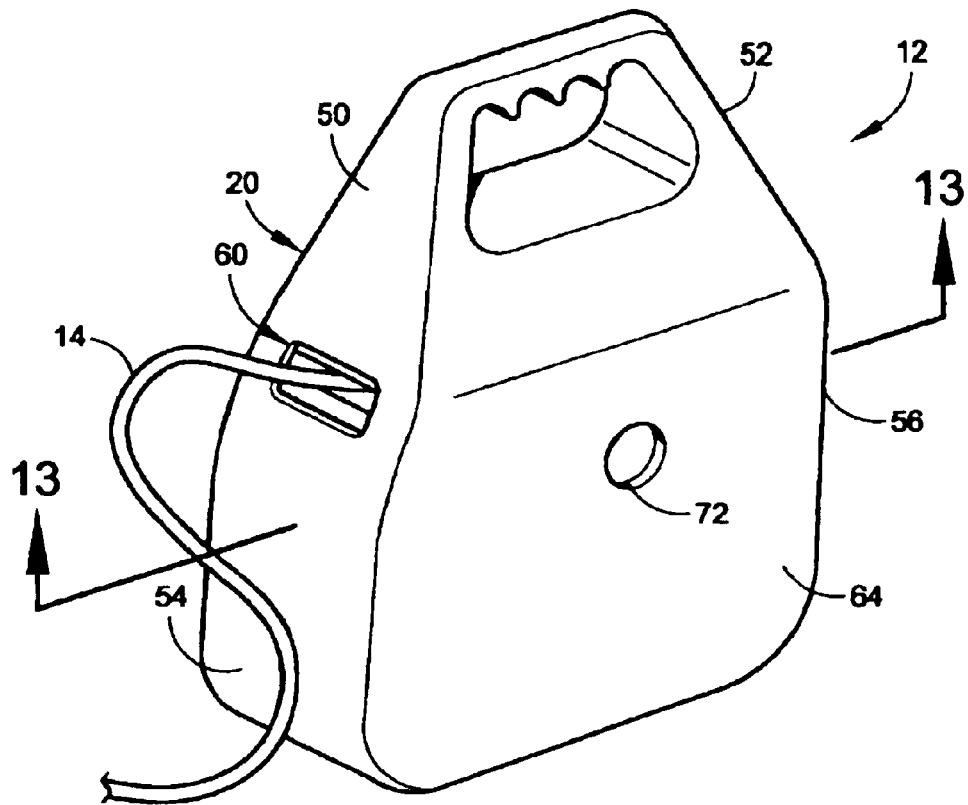
FIG. 1 is a perspective view of a coupling mechanism, which is constructed in accordance with the present invention.

Referring now to the drawings and more particularly to FIGS. 1–4, thereof there is illustrated a portable air delivery system 10, which is constructed in accordance to one preferred embodiment of the present invention. The portable air delivery system 10 is lightweight and can be easily carried or transported with a user thereby allowing an oxygen dependent user to freely move in any desired direction relative to a heavy and burdensome canister of air 11.

Considering now the portable air supply system 10 in greater detail with reference to FIGS. 1–4, the air delivery system 10 includes a coupling mechanism or an oxygen air tube reel assembly 12 having a stationary tube coupler 18 and an extendible length of oxygen tubing 14 that can be paid out or taken up over a predetermined length to give a user a wide range of mobility. The coupling mechanism 12 is adapted to be connected between a source of oxygen-enriched air, such as the air canister 11 and an air cannula 16 that can be worn by a user. The stationary tube coupler 18 facilitates coupling the air cannula 16 to the coupling mechanism 12 by a fixed length of oxygen tubing 13 that is sufficient long to allow the air cannula 16 to be comfortably worn by a user. The distal end of the extendible length of tubing 14 is coupled to the air canister 11 in such a manner so that the oxygen tubing 14 can be extended or retracted in length by the coupling mechanism 12 as the user moves in different directions from the air canister 11. In this regard, the coupling mechanism 12 is adapted for paying out and for winding up the predetermined length of tubing 14 without causing the air cannula to be dislodged from the user.

Figure 5:
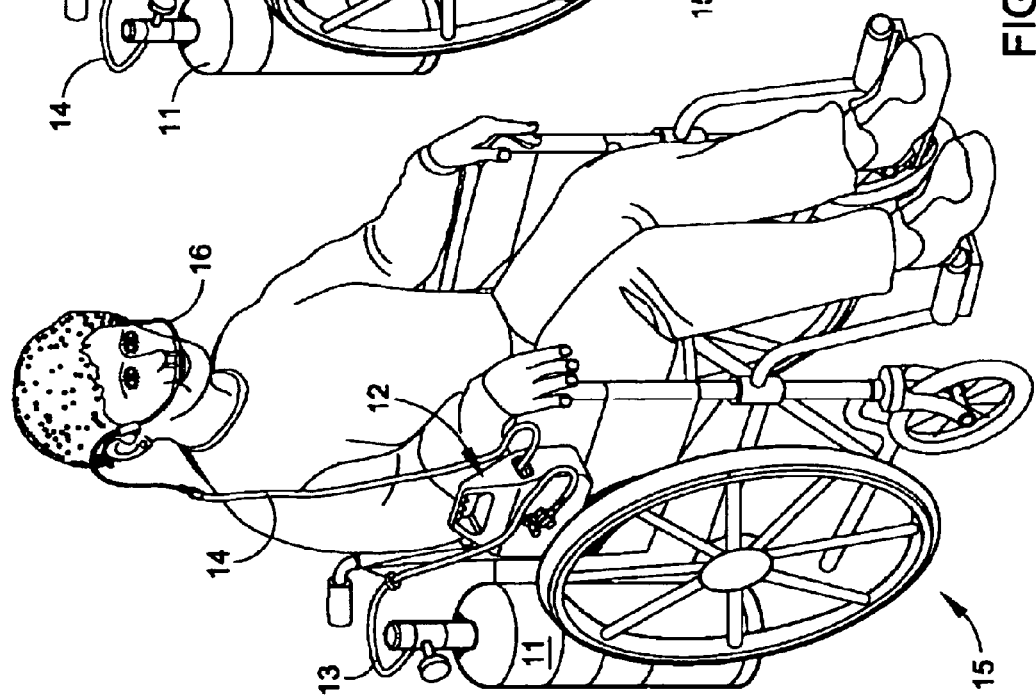
FIG. 5 is a perspective view of another air delivery system utilizing the coupling mechanism of FIG. 1.

Although in the preferred embodiment of the present invention, the coupling mechanism 12 is shown being worn on the belt of the user, it is contemplated that the coupling mechanism 12 may also be hand carried by a user or mounted on a stationary device such as a bed in close proximity to a hospital air supply system or on a mobile device, such as a wheelchair 15 that is adapted to carry a large portable supply of air under pressure as best seen in FIG. 5. In this alternative embodiment, an air delivery system 210 includes a coupling mechanism 12 with reversed connections so that the fixed length of oxygen tubing 13 is coupled to the air canister 11, while the predetermined length of oxygen tubing 14 is coupled to the air cannula 16. In this configuration it should be understood by those skilled in the art that the coupling mechanism 12 has a sufficiently low drag factor to allow complete mobility of a user wearing the cannula 16 without causing the cannula 16 to be dislodged during pay out of the predetermined length of tubing and without causing the cannula 16 to be dislodged during take up of the predetermined length of tubing.

Considering now the coupling mechanism 12 in still greater detail with reference to FIGS. 1–4, in use, an oxygen dependent user attaches the coupling mechanism 12 to his or her belt, and then connects the coupling mechanism 12 between the source 11 of oxygen-enriched air and the user worn air cannula 16. In this regard, the output side of the oxygen air tube reel 12, namely a length of its wound up tubing 14 is pulled out a sufficient distance to allow the free end of the tubing 14 to be connected to the air canister 11. Then a fixed length of tubing 13, sufficient to reach from the air cannula 16 to the stationary coupling device 18, is coupled between the coupling device 12 and the air cannula 16. The airflow from the air canister 11 is then activated, in order to allow the user or an assistant to verify that the flow of air is constant and is reaching the air cannula 16. Once the user or assistant has verified that air is flowing freely to the air cannula 16, the user attaches the air cannula 16 in a proper manner to the head of the user that ensures the airflow will reach the lungs of the user.

Thereafter, whenever the user desires to move away from the air canister 11, the user simply leaves the transportation device 15 carrying the reel 12 on his or her person. In this regard, as the user moves away from the air canister 11, the coupling mechanism 12 pays out its wound air tubing 14 at a sufficient rate, as will be described hereinafter in greater detail, so as not to cause any unwanted and undesired drag against the person of the user. Whenever the user decides that he or she desire to return to the transportation device 15, the user moves towards the device 15 and by doing so the drag tension on the tubing 14 is sufficient to allow the tubing 14 to be wound up within the mechanism 12 at a sufficient rate to allow its take up without causing any excess tubing to become tangled in an interfering manner with the user.

When using the coupling mechanism 12 in the alternative air delivery system 210, the coupling mechanism 12 is mounted to the stationary device or mobile device, such as the wheelchair 15 and the then the couplings to the mechanism 12 relative to the source 11 of air under pressure and the air cannula 16 are reversed. In this regard, the fixed length of oxygen tubing 13 is connected between the source 11 of air under pressure and the stationary tube coupler 18, while the extendible oxygen tubing 14, is connected or coupled to the air cannula 16 as best seen in FIG. 5.

Figure 2:
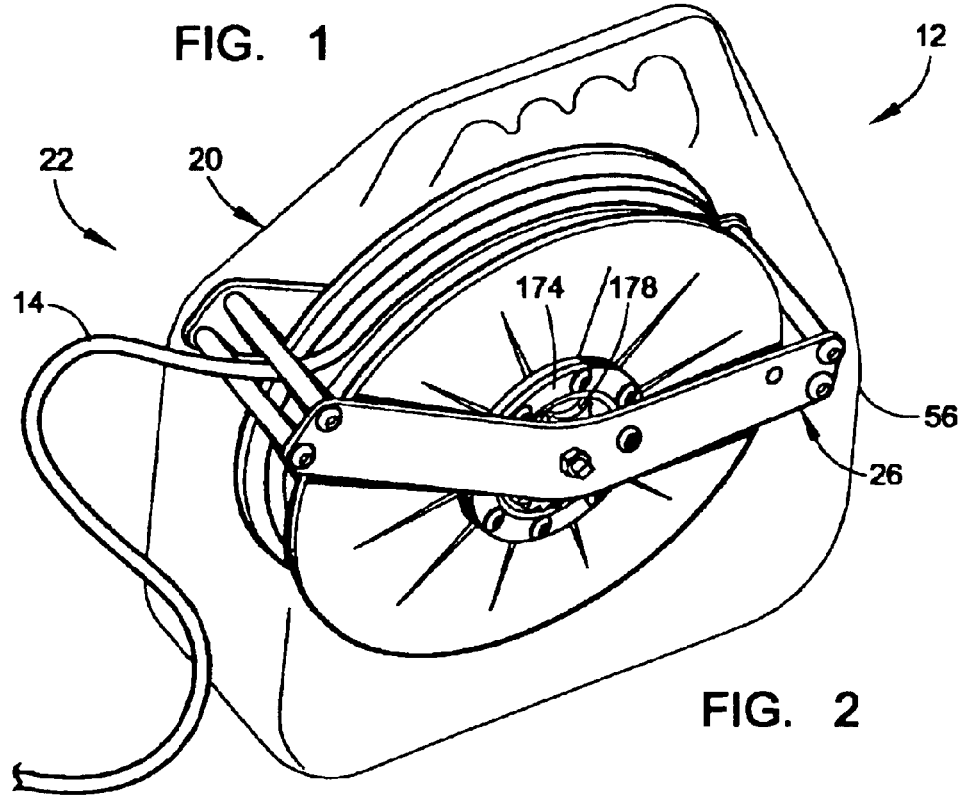
FIG. 2 is a cutaway view of the coupling mechanism of FIG. 1 illustrating a spool assembly for payout and take up of a predetermined length of oxygen tubing.
Figure 3:
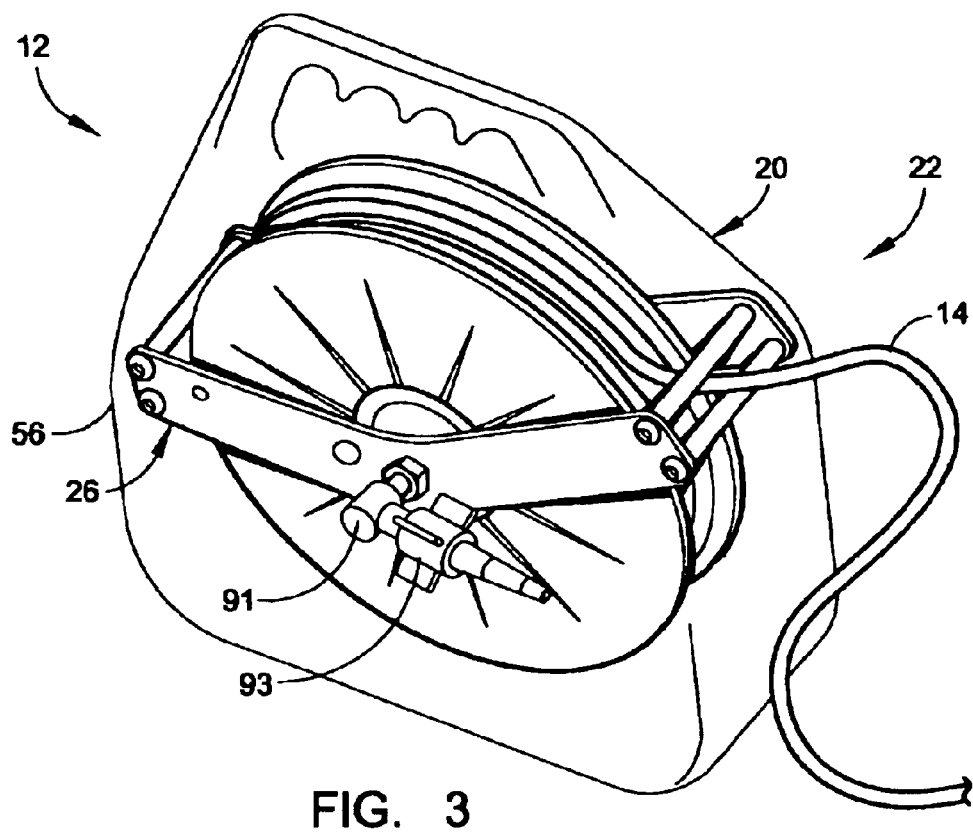
FIG. 3 is another cutaway view of the coupling mechanism of FIG. 1 with the coupling mechanism rotated in the horizontal plane by 180 degrees.
Figure 12:
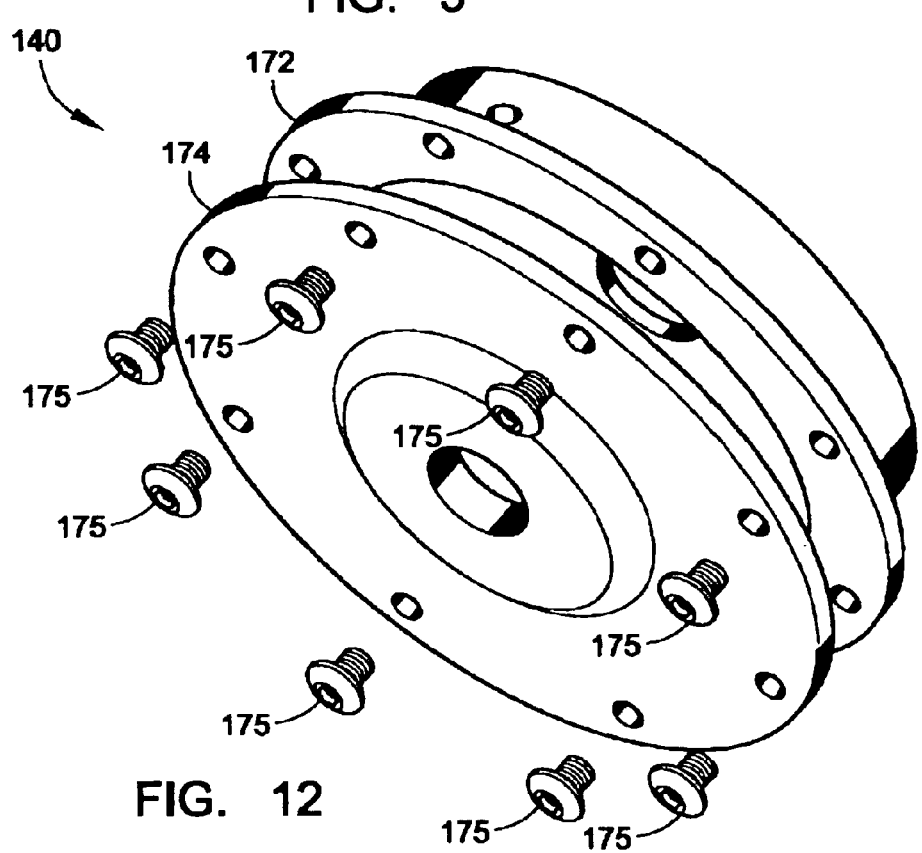
FIG. 12 is an exploded view of the return spring assembly of FIG. 10.
Figure 4:
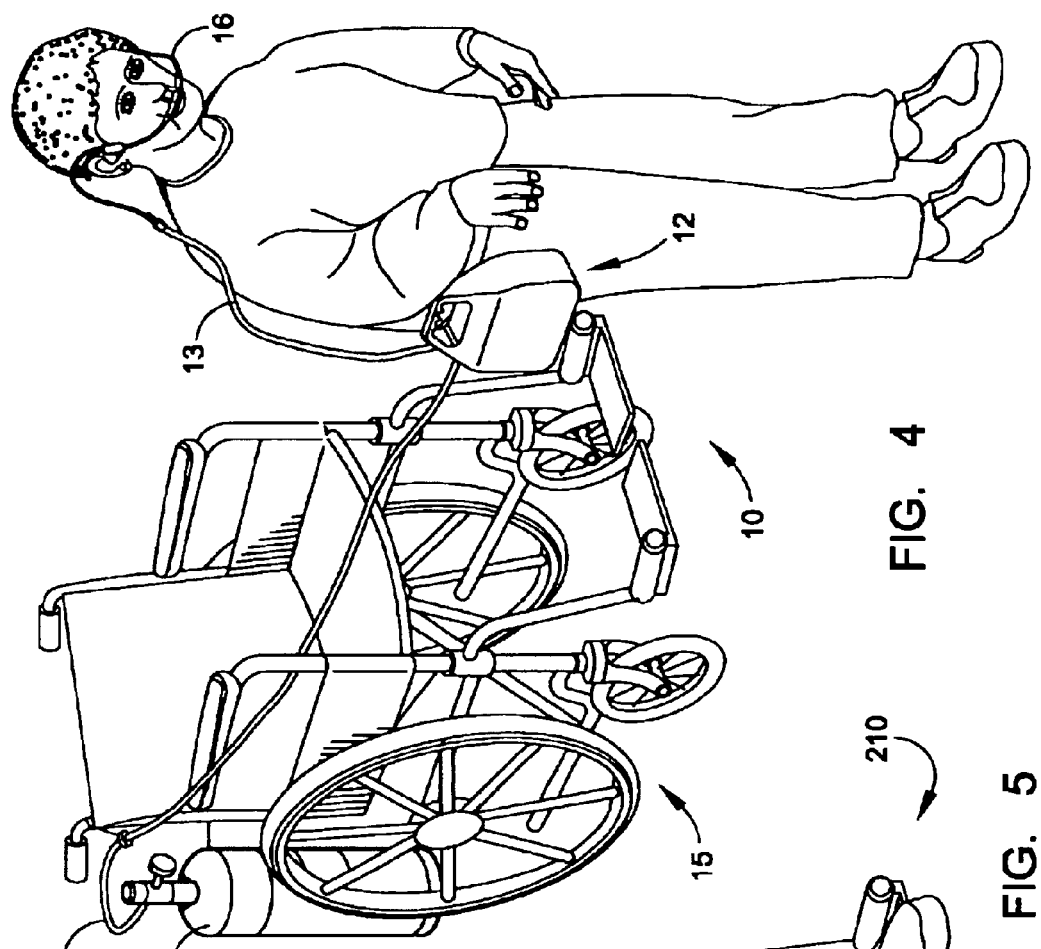
FIG. 4 is a perspective view of an air delivery system utilizing the coupling mechanism of FIG. 1.
Figure 6:
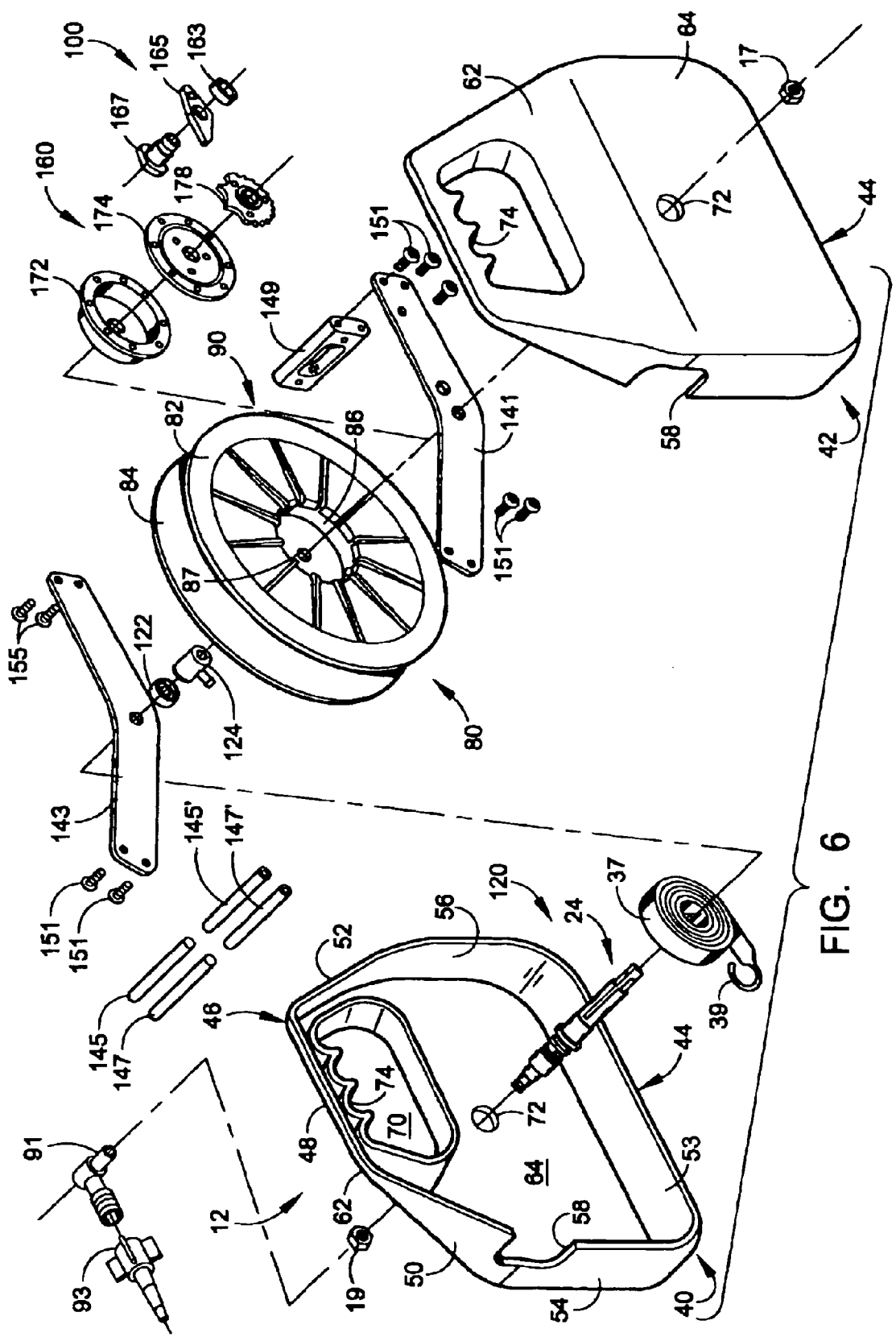
FIG. 6 is an exploded view of the coupling mechanism of FIG. 1.

Considering now the oxygen air tube reel 12 in greater detail with reference to FIGS. 14 and 6, the portable, light weight tube reel 12 generally includes a housing or carrying case 20 that is adapted to be worn (or carried) by the user as best seen in FIG. 4 or mounted to the transportation device 15 as best seen in FIG. 5. The interior of the housing 20 has a sufficiently large volume to hold therein a spool assembly 22 as best seen in FIGS. 2–3. The spool assembly 22 contains or has wound up thereon, a predetermined amount of oxygen tubing, such as the oxygen tubing 14 as best seen in FIGS. 2–3. The spool assembly 22 is supported within the housing 20 for rotational movement on an elongated axle 24 that is fixedly mounted to a yoke or tube guide assembly 26 by a set of push on nuts 17 and 19. The yoke assembly 26 is structured in such a manner to allow it and the spool assembly 22 to be wedged in a fixed position within the housing 20 as best seen in FIGS. 2–3.

Figure 7:
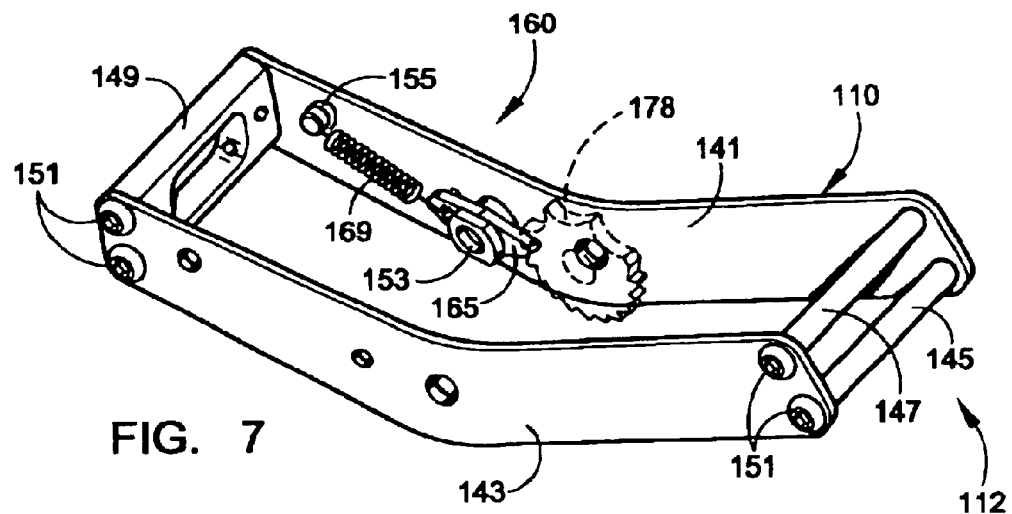
FIG. 7 is a perspective view of a yoke assembly of FIG. 3.
Figure 8:
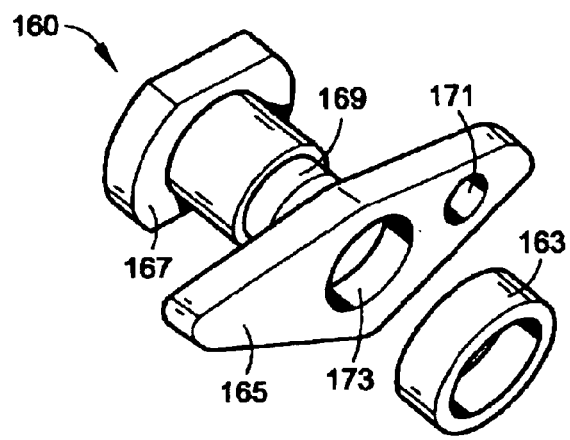
FIG. 8 is an exploded view of a latch assembly of FIG. 7.

Considering now the yoke assembly 26 in greater detail with reference to FIG. 7, the yoke assembly 26 generally includes a frame 110 that carries and supports relative to the spool assembly 22 a tube guide assembly 112 and a spring loaded latch assembly 160. The tube guide assembly 112 helps to facilitate the smooth payout and uptake of the tube 14 so that the tubing 14 is evenly wound on the spool assembly 22. The spring loaded latch assembly 160, as will be explained hereinafter in greater detail, interacts with the spool assembly 22 to help maintain a uniform drag on the tubing 14 as it pays out and then permits the tubing 14 to be taken up when the user causes the latch assembly 160 to be released.

Considering now the yoke assembly 26 in still greater detail, the frame 110 includes a pair of V-shaped bent yoke arms 141 and 143 that are spaced apart at one end by tube guide assembly 112 and at the other end by a spacer 149. The tube guide assembly 112 as well as the spacer 149 is mounted to yoke arms 141 and 143 respectively by screws 151. As best seen in FIG. 7, the spring loaded latch assembly 160 is mounted between a pair of mounting posts 153 and 155 respectively, which extend perpendicularly outward from the support arm 141.

As noted earlier, the spring loaded latch assembly 160 is mounted to the interior wall of the yoke arm 141 and is located to interact with a locking sprocket assembly 100 that forms part of the spool assembly 22 as will be described hereinafter in greater detail. The latch assembly 160 generally includes a spacer 163, a latch arm 165 and a securing nut 167 that is received on the post 153 to secure the spacer 163 and arm 165 to the post 153 as well. A spring 169 extends from a spring mounting post 155 and is attached at its distal end to a hole 171 in the latch arm 165. The latch arm 165 further includes a centrally located hole 173 that has a diameter slightly larger than a distal end 169 of the nut 167 thereby allowing the distal end 169 of the nut 167 to pass through the hole 173 and the interior of the spacer to secure both the spacer 163 and the latch arm 165 to the latch mounting post 153.

Considering now the tube guide assembly 112 in greater detail, the tube guide assembly 112 generally comprises a pair of steel sleeve members 145 and 147 that carry soft rubber like rollers 145' and 147' respectively. The rollers 145 and 147 are sufficiently spaced apart to permit the oxygen tubing 14 to pass between them and to be guided in a side to side motion as the tubing 14 causes the roller 145 and 147 to rotate as the tubing 14 is paying out or is being taken up relative to the spool assembly 22. This side-to-side motion permits the tubing 14 to be even wound onto the spool assembly 22.

Considering now the spool assembly 22 in greater detail with reference to FIGS. 2–3 and 6, the spool assembly 22 is supported within the housing 20 by the yoke assembly 26 (FIG. 7) and generally includes a spool 80, the locking sprocket assembly 100, an air outlet port assembly 120 and a spring loaded axle assembly 140 that cooperate with one another to help facilitate payout and uptake of the tubing 14 while maintaining an air tight seal between the air source 11 and the coupling mechanism 12. The spool 80, the locking sprocket assembly 100, and the air outlet port assembly 120 are all mounted on the axle 24 as will be explained hereinafter in greater detail.

Figure 10:
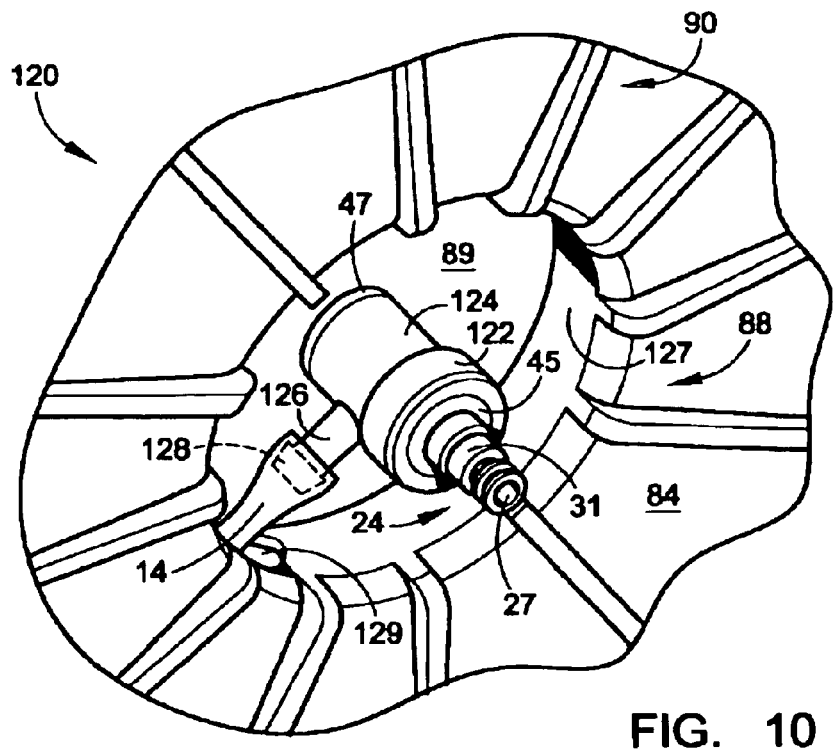
FIG. 10 is an enlarged view of the air manifold assembly of FIG. 6.
Figure 11:
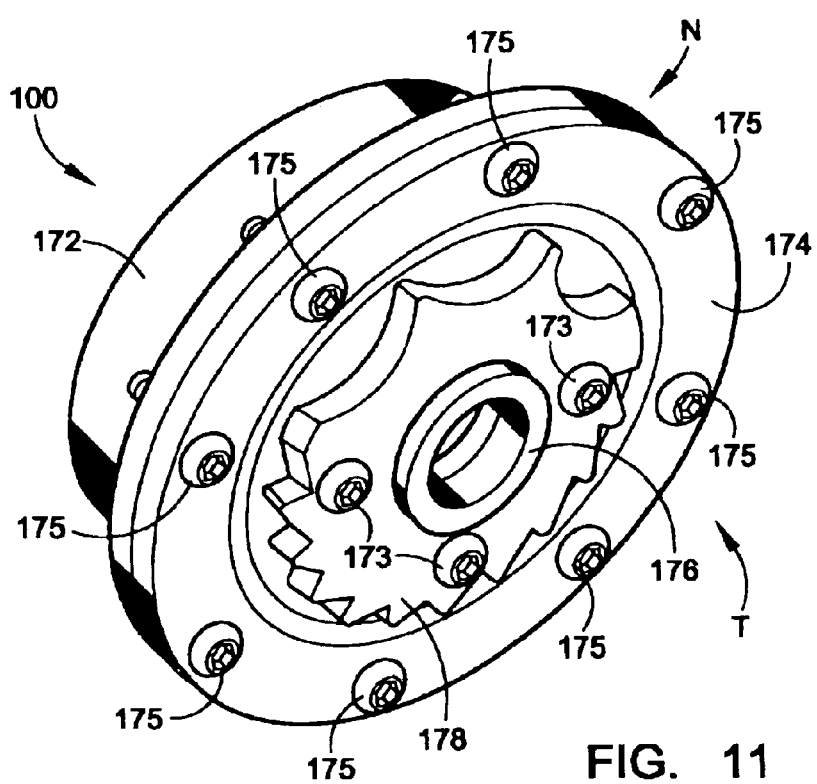
FIG. 11 is an enlarged perspective view of the return spring assembly of FIG. 6.
Figure 13:
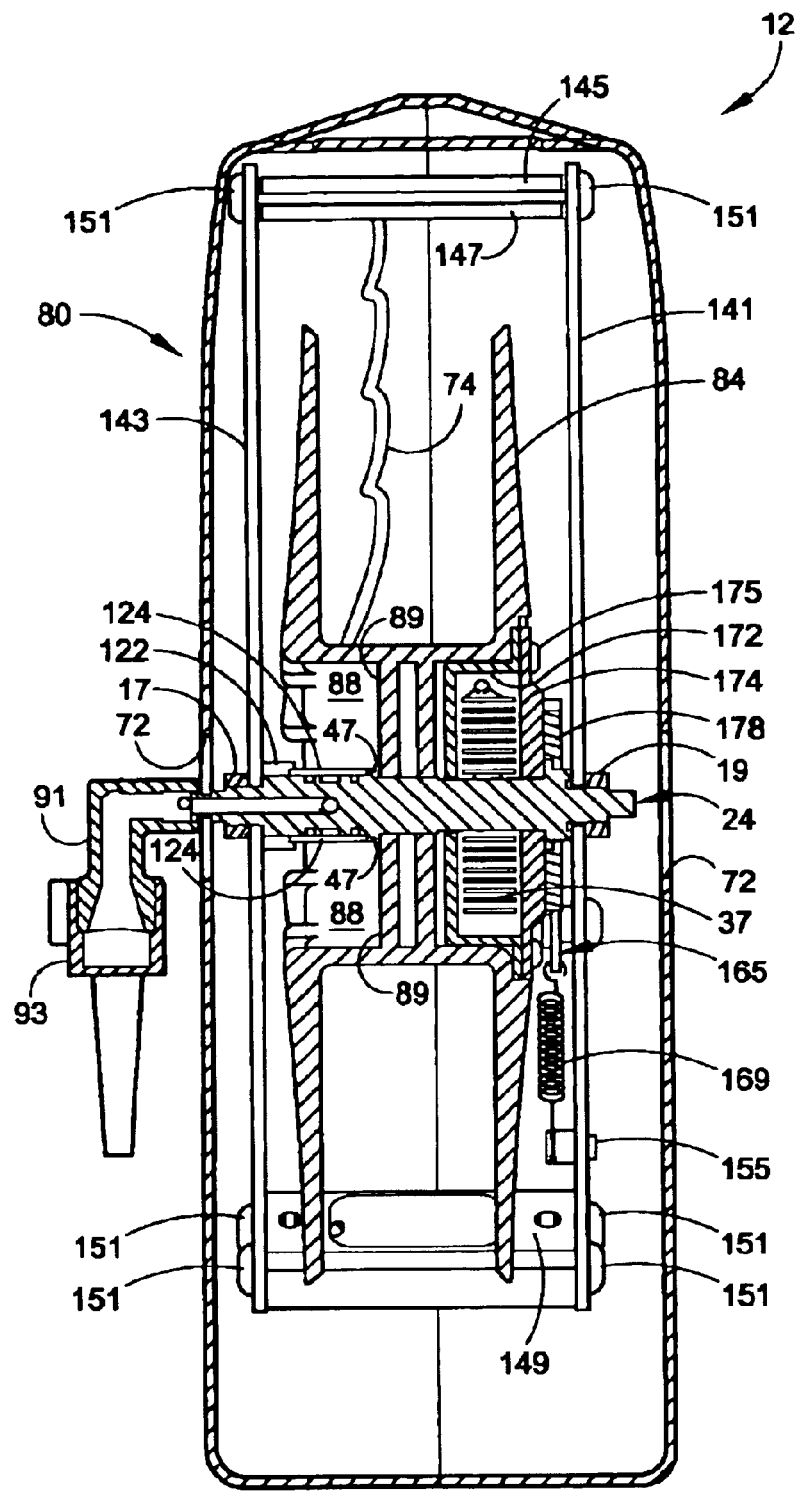
FIG. 13 is a cross sectional view of the coupling mechanism of FIG. 1 taken along line 13—13.

Considering now the spool 80 in greater detail with reference to FIGS. 6, 10 and 11, the spool 80 has a sufficient diameter and width dimension to hold between about 50 feet of oxygen tubing and about 100 feet of oxygen tubing. The spool 80 includes a right hub 82 and a left hub 84 each having a centrally disposed well, such as a right side well 86 and a left side well 88. Each of the wells 86 and 88 have centrally disposed holes, such as a hole 87 that are dimensioned for cooperating with the axle 24 to support the spool 80 for rotational movement. A set of spoke like protuberances, such as the protuberances indicted generally at 90 that extending radially outwardly from their respective wells 86 and 88 to help structurally balance the spool 80. The protuberances also help to retain the locking sprocket assembly 100 within the well 86 as will be explained hereinafter in greater detail.

Considering now the air output port assembly 120 in greater detail with reference to FIG. 10, the air output port assembly 120 generally includes a circular spacer 122 and tube coupler 124. The circular spacer 122 has an elongated cylinder like structure having a first inside diameter dimension sufficient to be received on a spacer-receiving segment 45 of the axle 24 and a second inside diameter dimension sufficient to capture the tube coupler 124 between the axle 24 and the spacer 122. An O-ring 125 is mounted on the axle 24 at about the junction of the spacer 122 and the tube coupler 124 to establish an airtight seal between them.

As best seen in FIG. 10, the tube coupler 124 is an elongated hollow cylinder having an integrally attached upstanding air tube spout 126. The distal end of the spout 126 includes a oxygen tube receiving tapered portion 128 that is dimensioned for receiving on thereon in a friction tight and air tight fit the proximal end of the tubing 14. The well 88 includes a sidewall 127 having a hole 129 disposed therein to allow the proximal end of the tubing 14 to pass from the interior of the spool 80 into the interior of the well 88. In this manner the proximal end of the tubing 14 is secured to the distal end 128 of the spout 126. The interior diameter of the tube coupler 124 is dimensioned to permit rotational movement of the tube coupler 124 relative to the axle 24. As noted earlier, the O-ring 125 is mounted on the axle 24 at about the junction of the spacer 122 and the tube coupler 124 or between segments 41 and 45 to establish an airtight seal between the spacer 122 and the tube coupler 124. Another O-ring 131 is mounted on the axle 24 at about the opposite end of the tube coupler 124 between segments 43 and 47 to provide an airtight seal at the opposite end of the coupler 124 as wall. In this manner air can pass under pressure and without leaking through the interior passageway 37 of the axle, up the spout 126 and into the tubing 14 regardless of whether the spool assembly 22 is rotating or is stationary. In short, this mounting arrangement assures the integrity of the airtight coupling between the oxygen air tube reel 12 and the air source 11.

More particularly, the manner in which the air outlet port assembly 120 is mounted within the wall 88 and on the axle 24 is an important feature of the present invention. In this regard the outlet port assembly 120 is mounted on the segment spacers 41 and 43 of the axle between the spacer segment 45 and the stop segment 47 for free rotational movements. With this arrangement as the spool 80 rotates for paying out or taking up the oxygen tubing 14, the tube coupler 124 rotates in unison with the spool 80. The rotation of the tube coupler 124 in response to the rotation of the spool 80 helps maintain the airtight seal between the proximal end of the oxygen tubing 14 and the distal end 128 of the port assembly 120.

Figure 9:
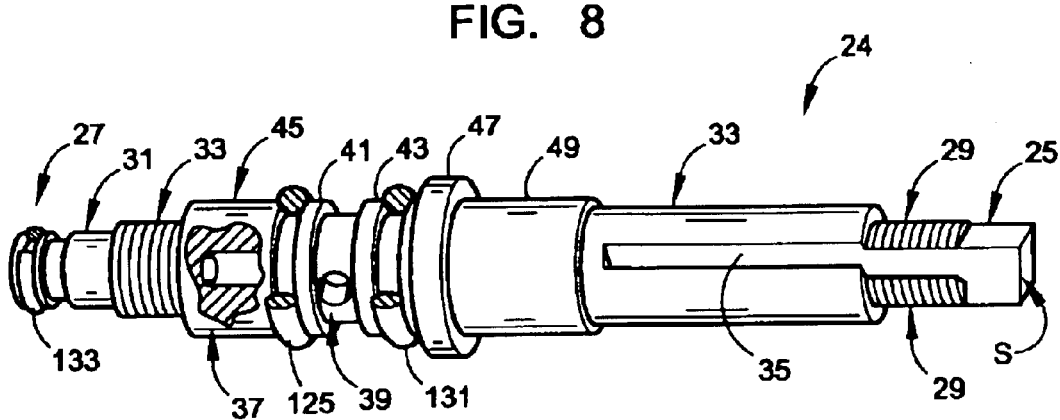
FIG. 9 is a greatly enlarged view of a spool axle of FIG. 6.

Considering now the axle 24 in greater detail with reference to FIG. 9, the axle 24 generally is a segmented spindle S that is hollow along part of its longitudinal axis starting at the air input port mounting end 27 and extending to an air outlet port 39 for defining an air passageway indicated generally at 37. The air output port 39 is disposed between a pair of upstanding separator segments 41 and 43 respectively. The separators 41 and 43 are sandwiched between a spacer receiving segment, indicated generally at 45, and an air outlet port stop segment 47. The outlet port stop segment 47 has a diameter that is greater than the diameter of hole 87. In this regard, when the axle 24 is passed through the hole 87 to permit the air input port mounting end 27 to be received within the well 88, the outlet port stop segment 45 functions as a stop to limit the travel of the mounting end 27 relative to the inner face of the well 88.

Considering now the spring loaded axle assembly 140 in greater detail with reference to FIGS. 6 and 9, the spring loaded axle assembly 140 includes a leaf spring 37 (FIG. 6) and the spindle like axle 24 (FIG. 9). The axle 24 is an elongated segmented spindle having a square yoke mounting end 25 and a round air input port mounting end 27. A set of nut capture protuberances, indicated generally at 29, is disposed adjacent to the mounting end 25. In this regard, the push on nut 17 as best seen in FIG. 6 is received over the mounting end 25 and onto the protuberances 29 to secure the axle 24 at one of its ends to the yoke assembly 26. The axle 24 also includes a nut guide segment 31 and a nut-mounting segment, indicated generally at 33, which is disposed adjacent to the nut guide segment 31. The nut-mounting segment 33 is dimensioned to receive thereon in a friction tight fix the nut 19 for securing the opposite end of the axle 24 to the yoke assembly 26. In this regard,, the push on nut 19 is received over the mounting end 27 onto the nut guide 31 and then onto the nut mounting segment 33 to secure the axle 24 at the other one of its ends to the yoke assembly 26. With this mounting arrangement the air outlet port assembly 120 is captured between the yoke arm 141 and a back wall 89 of the well 88.

As best seen in FIG. 9, the set of protuberance 29 terminate at a spring capture segment indicated generally at 33 that includes a spring receiving key way 35. The proximal end of the leaf spring 37 includes an open eye hook 39 that wrapped around the spring capture segment 33 and captured by its proximal end within the key way 35. The leaf spring 37 is wound around the axle 24 a sufficient distance so that the distal end of the leaf spring 37 can be attached to the locking sprocket assembly 100 as will be explained in greater detail hereinafter.

Considering now locking sprocket assembly 100 in greater detail with reference to FIG. 11, the locking sprocket assembly 100 generally includes a hub mount 172, a sprocket mounting plate 174, a sprocket spacer 176 and a sprocket 178. The sprocket 178 is secured to the sprocket plate 174 by a set of sprocket mounting screws, such as the screws 173 while the sprocket mounting plate 174 is secured to the hub mount 172 by another set of screws, such as the screws 175. The sprocket 178 includes a plurality of sprocket teeth, such as the teeth indicated generally at T and a plurality of nulls indicated generally at N. There are a sufficient number of teeth T to help facilitate the uniform payout of the tubing 14. To release the tension on the tubing 14 so the tubing 14 can be taken up onto the spool assembly 22, the user grasps the tubing at about its exit point from the housing 20 and pulls the tubing 14 out from the housing a sufficient distance to allow the latch 165 to engage a null. The tubing 14 is then released, which in turn allows the locking sprocket assembly 100 to rotate in an opposite direction at a uniform rate permitting the tubing 14 to be taken up on the spool 80.

Considering now the housing 20 in greater detail with reference to FIG. 6, the housing 20 generally consists of two half housing pieces 40 and 42 respectively. The half housing pieces 40 and 42 are the mirror images of one another. Each piece, such as piece 40, includes a reel supporting U shaped base portion indicated generally at 44 and an arch shaped top handle portion indicated generally at 46. Since the two half housing pieces 40 and 42 are substantially identical in construction, only the housing piece 40 will be described hereinafter in greater detail.

Considering now the half housing piece 40 in greater detail with reference to FIG. 6, the top handle portion 46 includes a bridge 48 that extends between spaced apart triangularly shaped upper front and upper back walls 50 and 52 respectively. The upper front wall 50 and the upper back wall 52 both slope outwardly away from each other at opposite ends of the bridge 48 and terminate in opposite facing upstanding base connecting walls, that include a lower front wall 54 and a lower back wall 56, each of which forms part of the reel supporting base portion 44.

The upper front wall 50 and the lower front wall 54 are integrally connected, as are the upper back wall 52 and the lower back wall 56. In this regard, walls 54 and 56 extend downwardly from their corresponding upper front wall 50 and upper back wall 52 respectively. The walls 54 and 56 are integrally connected at their base by a bottom wall 53.

A notch or cutout portion 58 is disposed in the upper front wall 50 at about where the upper front wall 50 and its corresponding lower front wall 54 are integrally connected. In this regard when the two half housing pieces 40 and 42 are joined to one another, the notches 58 form a rectangularly shaped opening 60 as best seen in FIG. 1. The opening 60 provides access to the open interior of the housing 20 and functions as a tube outlet port.

Considering the half housing piece 40 in still greater detail, the bridge 48 and the upper front wall 50 and the upper back wall 52 are further integrally connected to an outwardly sloping upper side wall 62 that extends outwardly from the side of the bridge 48 and terminates in an upstanding lower side wall 64 that also forms part of the reel supporting base portion 44.

A rectangularly shaped opening 70 in the sidewall 62 is disposed below the bridge 48 between the upper front wall 50 and the upper back wall 52. In this regard, the bridge 48 cooperates with the opening 70 to function as a handle when the two half pieces 40 and 42 of the housing 20 are joined. In this regard, the opening 70 has a finger grip structure 74 and is sufficiently large to accomodate the fingers and a portion of the hand of a user desiring to transport the housing 20.

As best seen in FIG. 1, the lower sidewall 64 is integrally connected between the lower front wall 54 and the lower back wall 56 respectively. The lower side wall 64 also has a centrally disposed circular opening 72 that is sufficiently large in diameter to accomodate the axle 24 that will be describe hereinafter in greater detail. The lower sidewall 64 and walls 54 and 56 respectively are further integrally connected at their bases to form the reel supporting base portion 44 in a U-shaped cup like configuration.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

I claim:

1. A tube reel, comprising:

a transportable housing;

a yoke wedged within said housing;

an elongated segmented spindle fixedly mounted to said yoke, said spindle having an air input port at one of its ends and an air output port disposed inboard of said air input port for defining an air passageway therebetween;

a spool assembly mounted for rotational movement on said spindle, said spool assembly having a sufficient diameter and width dimension for holding a predetermined length of wound up tubing; and a freely rotatable cylindrical tube coupler removable mounted on said segmented segment for free three hundred and sixty degree rotation about said segmented spindle at about said air output port;

wherein said housing includes a right side member and a left side member, said right side member and said left side member being adapted to be joined together to form a finger gripping handle at a top portion of said housing, a pair of oppositely disposed sidewall openings for providing interior access to said housing and a tube outlet port for helping to facilitate tube payout and retraction from an interior portion of said housing; and wherein said yoke includes a pair of spaced apart arms having a spacer disposed therebetween at one of their ends and a tube guide disposed therebetween at the other one of their ends to help facilitate side-to-side retracting motion of said tubing so that the tubing is evenly wound onto said spool assembly.

2. A tube reel according to claim 1, wherein one of said pair of arms includes a pair of spaced apart mounting posts extending perpendicularly outwardly therefrom for facilitating mounting therebetween a spring loaded latch assembly for helping to control rotational movement of said spool assembly.

3. A tube reel according to claim 2, wherein said spring loaded latch assembly includes:

a latch removably mounted to one of said pair of spaced apart mounting posts; and a spring extending between said latch and another one of said pair of spaced apart mounting posts, said spring cooperating with said latch and said yoke to hold said latch in tension with said spool assembly.

4. A tube reel according to claim 1, wherein said air output port is disposed between a pair of upstanding separator segments sandwiched between a spacer receiving segment and an air outlet port stop segment.

5. A tube reel according to claim 4, wherein said spool assembly comprises:

a spool for winding thereon between about 50 feet of tubing and about 100 feet of tubing;

said spool having a right hub with a centrally disposed spindle receiving well and a left hub with another centrally disposed spindle receiving well, wherein each well has a set of spoke like protuberances extending radially outwardly therefrom for helping to balance said spool during tubing payout and retraction;

a sprocket assembly disposed within said centrally disposed spindle receiving well for forward and reverse in unison rotation with said spool as said spool rotates about said segmented spindle;

said sprocket assembly including a circular sprocket having a given number of sprocket teeth separated by a given number of null, wherein said given number of, sprocket teeth is substantially larger than said given number of null to help facilitate uniform payout of said tubing; and wherein said sprocket and said latch are disposed in an engaging relationship to help facilitate the uniform payout and retraction of said tubing.

6. A tube reel according to claim 1, wherein said tube coupler includes an upstanding spout for receiving thereon a proximal end portion of said predetermined length of tubing and being removably mounted in an airtight fit relative to said segmented spindle to permit the free flow of air under pressure from said air output port to said proximal end portion of the tubing via said spout.

7. An air delivery system, comprising:

a transportable housing;

a frame wedged within said housing, said frame having a pair of spaced apart yoke arms;

a pair of spaced apart rollers disposed between said pair of spaced apart yoke arms at one of their ends;

a spacer disposed between said pair of spaced apart yoke arms at another one of their ends for helping to define a spool receiving space between said yoke arms;

a latch mount disposed on an interior surface of one of said arms;

a spring loaded latch disposed on said latch mount;

a elongated segmented spindle fixedly mounted between said pair of spaced apart yoke arms, said spindle having an air input port at one of its ends and an air output port disposed inboard of said air input port for defining an air passageway therebetween;

a spool mounted partially within said spool assembly receiving space on said spindle, said spool having a right hub and a left hub for defining a tube receiving space therebetween for holding a predetermined length of wound tubing;

a right side well disposed within said right hub;

a cylindrical sprocket assembly mounted within said right side well, said sprocket assembly having a sprocket and being dimensioned to position said sprocket spaced from said right hub a sufficient distance to facilitate latching engagement between said spring loaded latch and said sprocket;

a left side well disposed within said left hub; and a tube coupler mounted in said left side well, wherein said tube coupler includes an upstanding spout for receiving thereon a proximal end portion of said predetermined length of tubing and being removably mounted in an airtight fit relative to said segmented spindle to permit the free flow of air under pressure from said air output port to said proximal end portion of the tubing via said spout.

8. A tube reel assembly, comprising:

a frame positioned within a housing;

a segmented spindle fixedly mounted to said frame, said spindle having an air input port and an air output port, wherein said output port is disposed between two individual ones of a plurality of upstanding separator segments disposed on said spindle;

a spool mounted for 360 degree rotation about said spindle, said spool having a pair of hubs for holding therebetween a predetermined length of wound up tubing;

a tube coupler mounted for 360 rotation about said spindle and captured in an air-tight fit at about said air output port;

said tube coupler having an upstanding spout for receiving thereon a proximal end of said tubing for coupling said tubing to a source of air under pressure flowing from said air input port to said air output port;

wherein said frame includes:

a latch support arm having a spring loaded latch mounted thereto;

a tube guide support arm having one end of a tube guide secured thereto, wherein another end of said tube guide is secured at one end of said latch support arm; and spacer mounted at another end of said latch support arm and at another end of said tube guide support arm for cooperating with said latch support arm, said tube guide support arm, and said tube guide for defining a spool receiving space.

9. The tube reel assembly according to claim 8, wherein said segmented spindle is mounted fixedly between said latch support arm and said tube guide support arm.

* * * * *